US009840466B2

(12) United States Patent
Harichian et al.

(10) Patent No.: US 9,840,466 B2
(45) Date of Patent: Dec. 12, 2017

(54) PROCESS OF MAKING ADAMANTANAMIDES

(71) Applicant: Conopco, Inc., Englewood Cliffs, NJ (US)

(72) Inventors: Bijan Harichian, Brookfield, CT (US); Jose Guillermo Rosa, Cheshire, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/038,754

(22) PCT Filed: Dec. 4, 2014

(86) PCT No.: PCT/EP2014/076583
§ 371 (c)(1),
(2) Date: May 24, 2016

(87) PCT Pub. No.: WO2015/086428
PCT Pub. Date: Jun. 18, 2015

(65) Prior Publication Data
US 2017/0029375 A1 Feb. 2, 2017

(30) Foreign Application Priority Data
Dec. 9, 2013 (EP) .................... 13196213

(51) Int. Cl.
| C07D 211/16 | (2006.01) |
| C07D 215/08 | (2006.01) |
| C07D 217/06 | (2006.01) |
| C07C 231/02 | (2006.01) |
| C07D 205/02 | (2006.01) |
| C07D 207/06 | (2006.01) |
| C07D 211/62 | (2006.01) |
| C07D 295/185 | (2006.01) |

(52) U.S. Cl.
CPC .......... *C07D 211/16* (2013.01); *C07C 231/02* (2013.01); *C07D 205/02* (2013.01); *C07D 207/06* (2013.01); *C07D 211/62* (2013.01); *C07D 215/08* (2013.01); *C07D 217/06* (2013.01); *C07D 295/185* (2013.01); *C07C 2603/74* (2017.05)

(58) Field of Classification Search
CPC .. C07D 211/16; C07D 211/62; C07D 215/08; C07D 217/06; C07D 295/185; C07D 207/06; C07D 205/02; C07D 231/02; C07C 2603/74; C07C 231/02
See application file for complete search history.

(56) References Cited

U.S. PATENT DOCUMENTS

| 3,352,912 A | 11/1967 | Prichard et al. |
| 4,985,403 A | 1/1991 | Narula et al. |
| 8,053,431 B2 | 11/2011 | Kilburn et al. |
| 2006/0057083 A1 | 3/2006 | Mathonneau |
| 2010/0273879 A1 | 10/2010 | Klug |

FOREIGN PATENT DOCUMENTS

| JP | 04308558 | 10/1992 |
| WO | WO2004089415 | 10/2004 |
| WO | WO2004089416 | 10/2004 |
| WO | WO2006119283 | 11/2006 |
| WO | WO2008054144 | 5/2008 |
| WO | WO2010117258 A1 | 10/2010 |

OTHER PUBLICATIONS

Lekishvili, CA 154:615619, abstract only of Oxidation Communication, 33(1), 104-124, 2010.*
Asano, Amphiphilic Organocatalyst for Schotten-Baumann-Type Tosylation of Alcohols, Organic Letters, Feb. 9, 2009, 1757-1759, vol. 11 No. 8, US.
Dubowchik et al., Amines That Transport Protons Across Bilayer Membranes: Synthesis, Lysosomal Neutralization, and Two-Phase pKa Values by NMR, The Journal of Organic Chemistry, Jan. 1, 1996, 4676-4684XP055117324, 61, No. 14, American Chemical Society, ., US.
Gueo et al., Synthesis of Novel Quaternary Ammonium Surgactants Containing Adamantane, Chinese Chemical Letters, 2012, 653-656-, 23, 6, Elsevier, ., US
Harte, Synthesis of x-chloroamides in water—Supplementary Information, Tetrahedron Letters, ., 1-6, ., US.
Harte, Synthesis of x-chloroamides in water, Tetrahedron Letters, Jun. 15, 2006, 6321-6324, 47.
Lambert et al., Heterocyclic Deformations from Molecular Enlargement, The Journal of Organic Chemistry, Sep. 1, 1982, 3890-3893XP055117452, 47, No. 20, American Chemical Society.
Morita, Water-solvent method for tosylation and mesylation of primary alcohols, Green Chem, Aug. 11, 2005, 711-715, 7, US.
Nakatsuji, Water Solvent Method for Esterification and Amide, Adv. Synth. Catal, 2006, 2057-2062, 348, JP.
Pappas, Selective acylation of polyamines with acid anhydrides and acid chlorides in water, Letter in Organic Chemistry, 2010, 539-541, vol. 7 No. 7, US.
Ridyard et al, Site Selective Oxidation of Tricyclo (3.3.1.1.) Decane(Adamantane) and Some of Its Derivatives Using Fungi of the Genus Absidia, The Journal of the Chemical Society, Perkin Transactions 2, Jan. 1, 1996, 1811XP055117485, No. 9, US.
Sawamura, Manufacture of carboxylic acid amides, Japan Kokai Tokkyo Koho, 1992, ., ., JP.
Search Report & Written Opinion in EP13196213, May 23, 2014.
Search Report & Written Opinion in PCTEP2014076583, Feb. 19, 2015.
Ridyard et al., Site selective oxidation of tricyclo [3.3.1.1 3,7] decane (adamantane) and some of its derivatives using fungi of the genus *Absidia*, Journal of the Chemical Society Perkin Trans. 2, 1996, pp. 1811-1819.

* cited by examiner

*Primary Examiner* — D M Seaman
(74) *Attorney, Agent, or Firm* — Ellen Plotkin

(57) ABSTRACT

An effective process of making adamantanamide, which process is fast, does not the use of organic solvents or labor-intensive isolation or purification of the product, by removal of organic solvent or by-products, and has improved yield and purity.

10 Claims, No Drawings

PROCESS OF MAKING ADAMANTANAMIDES

FIELD OF THE INVENTION

The present invention is directed to a method of making an adamantanamide.

BACKGROUND OF THE INVENTION

Adamantane derivatives, and in some cases adamantanamides, have been described. See for instance Kilburn et al., U.S. Pat. No. 8,053,431B2; WO2004/089415A2 (Novo Nordisk A/S); WO2004/089416A2 (Novo Nordisk A/S); Narula et al., U.S. Pat. No. 4,985,403; Mathonneau, US 2006057083; WO06/119283 (Hunton & Williams LLP); WO08/054144 (Amorepacific Corporation). Adamantanamides are known pharmaceutical agents, and have also recently become useful in cosmetic compositions.

Amides have been made by reacting carboxylic acid chlorides with primary or secondary amines (Schotten-Baumann-type reaction). In the first step an acid chloride reacts with an amine so that an amide is formed, together with a proton and a chloride ion. Addition of a base is required to absorb this acidic proton, or the reaction will not proceed. The name "Schotten-Baumann reaction conditions" is often used to indicate the use of a two-phase solvent system, consisting of water and an organic solvent. The base within the water phase neutralizes the acid, generated in the reaction, while the starting materials and product remain in the organic phase, often dichloromethane or diethyl ether. Having the base in a separate phase prevents the amine reactant from being protonated, which otherwise would be unable to react as a nucleophile.

See e.g. Klug et al., US 2010/0273879; Katsuhiko et al., JP04308558 ABS; Zainab et al., WO2010/117258A1; Asano et al., Amphiphilic Organocatalyst for Schotten-Baumann-Type Tosylation of Alcohols under Organic Solvent Free Condition, Organic Letters, Feb. 9, 2009, Volume 11, No. 8, pages 1757-1759; Harte et al., Synthesis of α-chloroamides in water, Supplementary Information, Tetrahedron Letters, pages 1-6; Harte et al., Synthesis of α-chloroamides in water, Tetrahedron Letters, Jun. 15, 2006, Volume 47, pages 6321-6324; Morita et al., Water-solvent method for tosylation and mesylation of primary alcohols promoted by KOH and catalytic amines, Green Chem., Aug. 11, 2005, Volume 7, pages 711-715; Nakatsuji et al., Water Solvent Method for Esterification and Amide Formation between Acid Chlorides and Alcohols Promoted by Combined Catalytic Amines: Synergy between N-Methylimidazole and N, N, N', N'-Tetramethylethylenediamine (TMEDA), Adv. Synth. Catal, 2006, Volume 348, pages 2057-2062; Pappas et al., Selective acylation of polyamines with acid anhydrides and acid chlorides in water, Letter in Organic Chemistry, 2010, Volume 7, No. 7, pages 539-541; Sawamura et al., *Manufacture of carboxylic acid amides*, Japan Kokai Tokkyo Koho, 1992.

Unfortunately, in the case of adamantanamides, the starting adamantane carbonyl chloride is a solid and the reaction requires an organic solvent, the use of which is undesirable: it may be toxic and/or flammable, and, in any event, requires removal at the end of reaction. If the starting adamantane carbonyl chloride is not solubilized, then the reaction takes a long time and is not efficient. Furthermore, the existing processes frequently result in the formation of by-products which also require complicated/labor-intensive removal.

SUMMARY OF THE INVENTION

The present invention includes a process of making an adamantanamide, the process comprising the steps:

i. mixing 0.9 to 1 molar equivalents of an alkylamine and 1.0-1.5 molar equivalents of a base in sufficient water to obtain a concentration of the alkylamine in the aqueous solution between 0.1 to 1.0 M and the pH between 8 to 14;

ii. heating the mixture to a temperature in the range of from 50° C. to 90° C., to obtain a heated aqueous basic solution of the alkylamine;

iii. adding 1 molar equivalent of adamantanecarbonyl chloride to the heated aqueous basic solution of alkylamine, to obtain a bi-phasic mixture;

iv. stirring the bi-phasic mixture of the alkylamine and the adamantanecarbonyl chloride and maintaining the temperature in the range of from 50° C. to 90° C., until the reaction is completed;

v. stirring and allowing the reaction mixture to cool to below 30° C., to precipitate the adamantanamide product out of the reaction mixture; and vi. separating the adamantanamide product from the reaction mixture.

The inventive process is fast, does not require labor-intensive isolation or purification of the product, adamantanamide, by removal of organic solvent or by-products, and has improved yield and purity.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about."

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

Adamantanamide

There is generally no limitation with respect to the adamantanamide that may be prepared according to the inventive process. The inventive process is most useful for the synthesis of 1-adamantamides, because out of many adamantane derivatives that can be used as starting materials to prepare adamantanamides, 1-adamantanecarbonyl chloride is the most common and is available commercially in bulk quantities. Upon reacting 1-adamantanecarbonyl chloride with an amine, 1-adamantanamides is obtained. Often, the adamantanamide prepared according to the inventive process is represented by a compound having Formula I or Formula II. Adamantanamides of Formula I are preferred, because they are generally more potent than those of formula II when tested against our biological targets of interest, leading to superior functional benefits.

Formula I

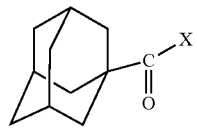

Where X is selected from:

Xa

-continued

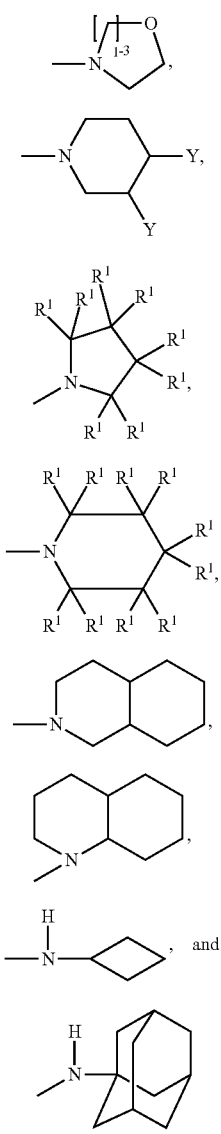

further wherein
t is an integer from 1 to 8; Y is hydrogen,

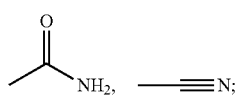

or a halogen
where each $R^1$ is independently a hydrogen or a $C_{1\ to\ 4}$ alkyl.

Preferably, X is selected from groups Xd, Xe, Xf, Xg, more preferably Xd and Xe, ideally X is selected from groups Xe and Xd, wherein $R^1$ is hydrogen on all but one carbon and is mono- or di-substituted on that single carbon with methyl or ethyl groups.

Preferred Formula I compounds, wherein X is selected from the group consisting of groups Xa, Xb, Xc, Xd, Xe, Xf, Xg, Xh, Xi are:

Methanone, (morphonyl)tricyclo[3.3.1.1$^{3,7}$]dec-1-yl- (C1)
Methanone, (piperidinyl)tricyclo[3.3.1.1$^{3,7}$]dec-1-yl- (C2)
Methanone, (pyrrolidinyl)tricyclo[3.3.1.1$^{3,7}$]dec-1-yl- (C3)
Methanone, (azetidinyl)tricyclo[3.3.1.1$^{3,7}$]dec-1-yl- (C4)
Methanone, (hexahydroazepinyl)tricyclo[3.3.1.1$^{3,7}$]dec-1-yl- (C5)
Methanone, (4-cyano-piperidinyl)tricyclo[3.3.1.1$^{3,7}$]dec-1-yl- (C6)
Methanone, (4-amido-piperidinyl)tricyclo[3.3.1.1$^{3,7}$]dec-1-yl- (C7)
Methanone, (Tricyclo[3.3.1.1$^{3,7}$]decanyl)-N-tricyclo[3.3.1.1$^{3,7}$]dec-1-yl- (C8)
Methanone, (decahydroisoquinolinyl)tricyclo[3.3.1.1$^{3,7}$]dec-1-yl- (C9)
Methanone, (decahydroquinolinyl)tricyclo[3.3.1.1$^{3,7}$]dec-1-yl- (C10)
Methanone, (3,3-dimethyl-1-piperidinyl)tricyclo[3.3.1.1$^{3,7}$]dec-1-yl- (C11)
Methanone, (2-methyl-1-piperidinyl)tricyclo[3.3.1.1$^{3,7}$]dec-1-yl- (C12)
Methanone, (4-methyl-1-piperidinyl)tricyclo[3.3.1.1$^{3,7}$]dec-1-yl- (C13)
Methanone, (3-methyl-1-piperidinyl)tricyclo[3.3.1.1$^{3,7}$]dec-1-yl- (C14)
Methanone, (3,5-dimethyl-1-piperidinyl)tricyclo[3.3.1.1$^{3,7}$]dec-1-yl- (C15)
Methanone, (4-methyl-4-ethy-piperidinyl)tricyclo[3.3.1.1$^{3,7}$]dec-1-yl- (C16)
Methanone, (3,3-diethyl-1-pyrrolidinyl)tricyclo[3.3.1.1$^{3,7}$]dec-1-yl- (C17)

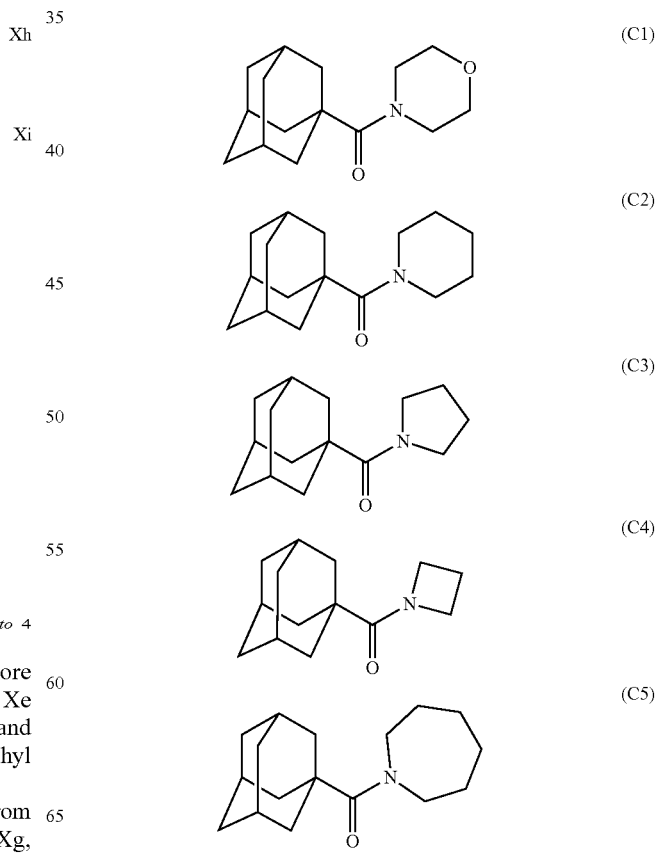

(C6) 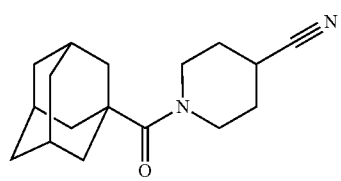

(C7) 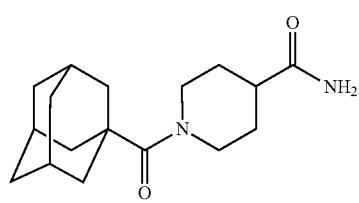

(C8) 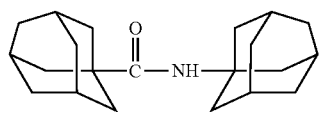

(C9) 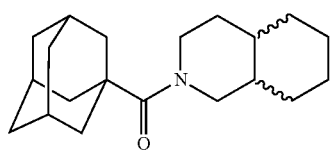

(C10) 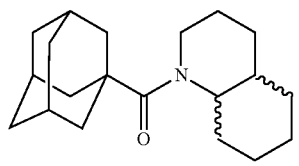

(C11) 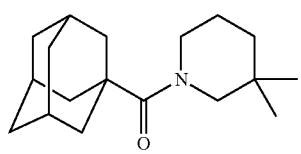

(C12) 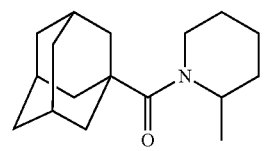

(C13) 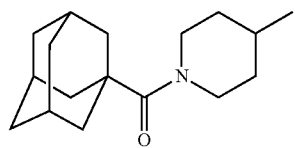

(C14) 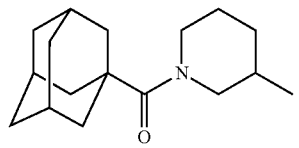

(C15)

(C16)

(C17)

More preferred compounds are compounds C9 through C17, and most preferred compounds are C11 through C17, optimally C14, due to the fact that these showed the highest potencies when tested against various biological targets of interest, leading to superior functional benefits.

Adamantanamides of Formula II, prepared according to the inventive process, have the following general structure:

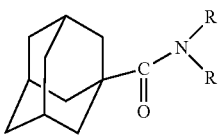

Formula II wherein each R is independently hydrogen, methyl, ethyl or a $C_3$ to $C_{18}$, preferably $C_3$ to $C_{10}$, (i.e. C3, C4, C5, C6, C7, C8, C9, C10) linear or branched alkyl, cycloalkyl or cyclo-heteroalkyl group, with the proviso that both R groups are not simultaneously hydrogen:

Methanone, (N,N-diisopropyl) tricyclo[3.3.1.1$^{3,7}$]dec-1-yl- (C18)
Methanone, (3,3-dimethylbutylaminyl) tricyclo[3.3.1.1$^{3,7}$]dec-1-yl- (C19)
Methanone, (2,2-dimethylpropylaminyl) tricyclo[3.3.1.1$^{3,7}$]dec-1-yl- (C20)
Methanone, (1,1-dimethyl-3,3-dimethylbutylaminyl) tricyclo[3.3.1.1$^{3,7}$]dec-1-yl- (C21)
Methanone, (1,3-dimethyl-butylaminyl) tricyclo[3.3.1.1$^{3,7}$]dec-1-yl- (C22)

(C18) 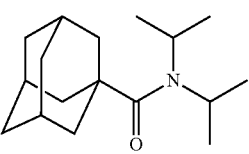

| | |
|---|---|
| (C19) 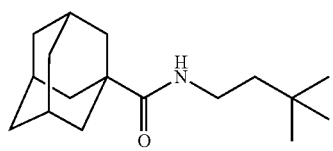 | |
| (C20) 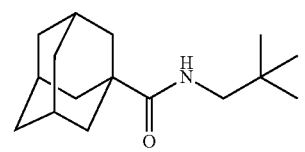 | |
| (C21) 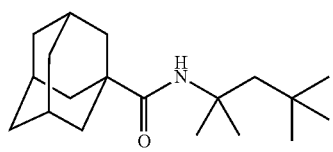 | |
| (C22) 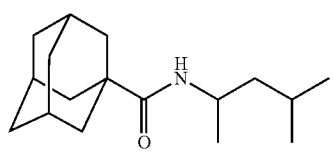 | |

Wherein compounds C19, C20, C21 and C22 are more preferred, and compounds C19 and C21 most preferred.

Inventive Process

Step (i) of the inventive process includes mixing an alkyl amine with an aqueous base solution. An alkyl amine may be secondary or primary, linear or branched or cyclic, substituted or unsubstituted. An alkyl amine is chosen such that the alkyl part of the alkyl amine will form the corresponding amide part of the desired adamantanamide.

Thus, for instance an alkyl amine for forming Xa through Xi is as follows:

| Alkyl Amine | X |
|---|---|
|  | Xa |
| 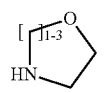 | Xb |
| 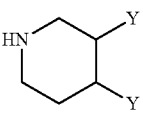 | Xc |
| 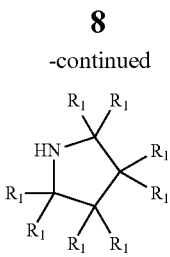 | Xd |
| 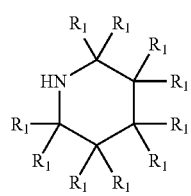 | Xe |
| 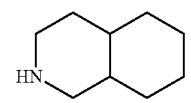 | Xf |
| 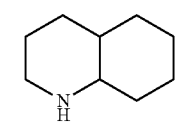 | Xg |
| 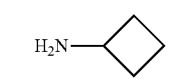 | Xh |
| 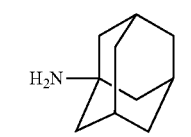 | Xi |

And more specifically, for Compounds C1-C17, an amine is:

| Amine | C |
|---|---|
| 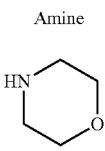 | C1 |
|  | C2 |
|  | C3 |
|  | C4 |
|  | C5 |

-continued

C6 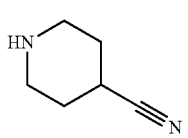

C7 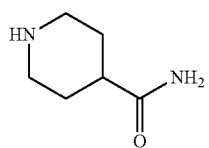

C8 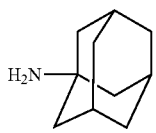

C9 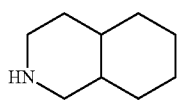

C10

C11 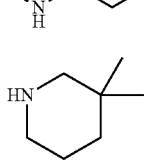

C12 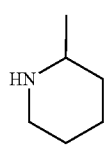

C13 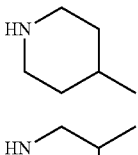

C14

C15 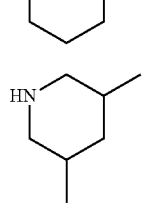

C16 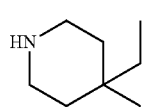

C17 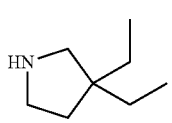

And in case of adamantanamides of Formula II, for Compounds C18-C22

Alkyl Amine | C

C18 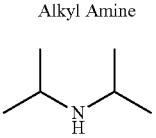

C19 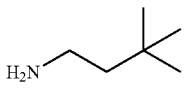

C20 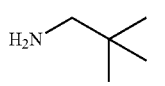

C21 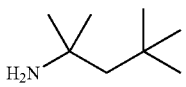

C22 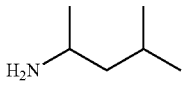

All amines suitable for inventive process are available from commercial sources.

A base that is used in step (i) of the inventive process may be organic or inorganic. Inorganic bases are preferred, because they are cost-effective and generate non-toxic salts.

Particularly preferred are sodium hydroxide, sodium carbonate and sodium bicarbonate, because they generate non-toxic sodium chloride as the only by-product in solution which is easily separated from the product via filtration. Sodium hydroxide is most preferred because it is the stronger base of the three, leading to more efficient reaction rates.

Other bases that could be used are the hydroxides, carbonates, bicarbonates and oxides of selected group I alkali metals (such as Li, K and Cs) and group II alkali earth metals such as (Mg, Ca and Ba); organic bases such as pyridine, alkoxides (methyl or t-butyl), triethanolamine The relative amounts of an alkyl amine and a base are such as to not have excessive starting ingredients upon reaction completion. According to the inventive process, 0.9 to 1 molar equivalent of an alkyl amine and 1.0 to 1.5 molar equivalents of a base, preferably 1.0 to 1.2 molar equivalents of a base. Most preferably, the molar equivalent ratio of an alkyl amine to a base is 1:1.

Sufficient water is used in step (i) of the inventive process to make the resulting aqueous solution of alkyl amine in the concentration of from 0.1 to 1.0 M, preferably from 0.5 to 1.0, most preferably from 0.7 to 1.0 and optimally from 0.8 to 1.0. The pH of the resulting aqueous solution of the alkyl amine is in the range of from 8 to 14, preferably from 9 to 14, most preferably from 10 to 14 and optimally from 10 to 12. The stronger the base, the higher the pH and the faster the reaction time.

In step (ii) of the inventive process, the aqueous base solution of alkyl amine, as obtained in step (i), is heated above the melting point of adamantane carbonyl chloride (its melting point is 49-51° C.). The temperature is typically in the range of from 50° C. to 90° C., preferably from 55° C. to 90° C. and most preferably from 55° C. to 80° C. This heated aqueous solution of alkyl amine is continuously stirred and to this solution, from 1 to 1.1 molar equivalent of adamantane carbonyl chloride is added. In a batch process, adamantane carbonyl chloride is added as a solid, gradually, with continuous vigorous stirring. In a continuous process, adamantane carbonyl chloride may be added as a pre-melted stream. Adamantane carbonyl chloride is commercially available, e.g. from Sigma-Aldrich. As a result of increased temperature of aqueous base solution of the alkyl amine, adamantane cabonyl chloride is maintained in a molten form and a biphasic mixture results: the first phase being the aqueous alkyl amine and the second phase an organic melted phase of adamantane carbonyl chloride. At this point, the temperature of the biphasic mixture may increase due to the exothermic reaction between alkyl amine and adamantane carbonyl chloride. The temperature is maintained in the range of from 50° C. to 90° C., preferably from 55 to 90, most preferably from 55° C. to 80° C. and in any event, temperature which is slightly above the melting point of adamantane carbonyl chloride, to maintain adamantane carbonyl chloride in molten form. This step of the process typically lasts from 15 minutes to 2 hours, preferably from 15 minutes to 1 hour, most preferably from 15 minutes to 30 minutes. Upon completion of the reaction, the reaction mixture is allowed to cool to room temperature, in any event temperature below 30° C., as a result of which the adamantanamide product is precipitated out of the reaction mixture. In the last step of the process, the precipitated product is isolated, by centrifugation or filtering, preferably by filtering.

The reaction mixture at the end contains adamantanamide (product), the chloride salt and adamantane carboxylate salt in water. Preferably the inventive process also comprises step (vii), wherein any residual adamantane carboxylate salt obtained from the filtrate or centrifugation is recycled and converted to adamantane carbonyl chloride.

The inventive process is advantageous, at least because it does not use any organic solvents, results in the minimal formation of by-products, if any, and is relatively fast. It also results in improved purity of from 90% to 99%, preferably from 95% to 99%, and most preferably at least 98% to 99%, and improved yield from 90% to 99%, preferably from 95% to 99%, and most preferably at least 98% to 99%.

EXAMPLES

Experimental Methods

All reagents and solvents were obtained from commercial sources and used without further purification.

Reaction Monitoring Methods

Thin layer chromatography using 10% ethyl acetate in hexanes and/or Gas Chromatography using boron trifluoride:methanol derivatization. For the latter method, reaction aliquots (100 microliters) are removed at various time points, processed by partitioning into 15% isopropanol in chloroform:1N hydrochloric acid (500 microliters:500 microliters), separating and evaporating the organic layer to a solid. The solid material (10 milligrams) is dissolved in boron trifluoride:methanol solution (1 milliliter), heated at 100° C. for 5 minutes, allow to cool to room temperature and diluted with hexane:water (2 milliliters:1 milliliter). The organic layer is separated/evaporated and the residue dissolved in acetone (1 milliliter) and diluted to 20 parts per million for gas chromatography analysis. Monitoring is done at various time points (0, 15, 30, 60, 120 minutes for example) to determine reaction completion.

Example 1

An example of the process within the scope of the invention was run.

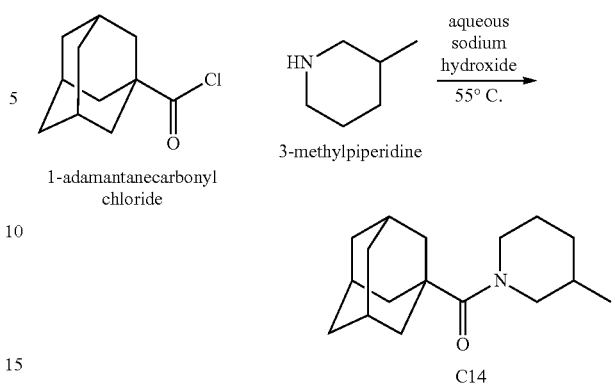

3-Methylpiperidine (59 milliliters, 0.5 moles) was added to a vigorously stirring solution of sodium hydroxide (20 grams, 0.5 moles) in water (622 milliliters) at 55° C., followed by slow addition of 1-adamantanecarbonyl chloride (90 grams, 0.5 moles), allowing it to melt upon addition. An exotherm of 10° C. (from 55° C. to 65° C.) was observed after complete addition of the acid chloride and the reaction composition consisted of a bi-phasic mixture (aqueous phase and melted organic phase). Gas chromatography monitoring showed reaction reached completion after 15 min. The mixture was allowed to cool to room temperature while stirring. The product crystallized as a white solid and filtered, washed sequentially with water, 0.5N hydrochloric acid, water and dried under high vacuum to give pure product (108 grams, 94% yield with >99% purity).

Comparative Example A

Room Temperature Process, Outside the Scope of the Invention:

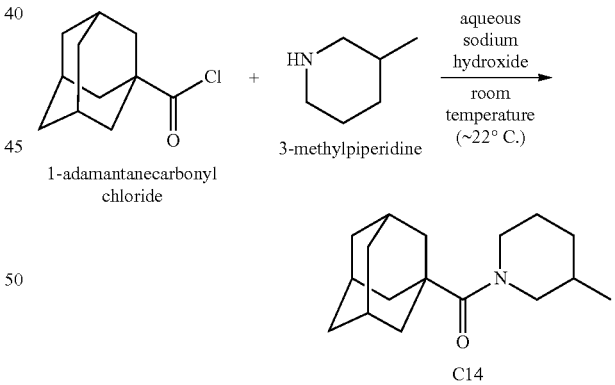

3-Methylpiperidine (2.68 milliliters, 0.023 moles) was added to a vigorously stirring solution of sodium hydroxide (1.06 grams, 0.026 moles) in water (33 milliliters) at approximately 22° C., followed by slow addition of 1-adamantanecarbonyl chloride (5 grams, 0.025 moles). An exotherm of approximately 5° C. (from 21.8° C. to 26.3° C.) was observed after complete addition of the acid chloride and the reaction composition consisted of a bi-phasic mixture (aqueous phase and oily-solid phase). The mixture was vigorously stirred at room temperature and monitored by gas chromatography for completion (approximately 24 hours). The product crystallized as a white solid and filtered, washed sequentially with water, 0.5N hydrochloric acid, water and dried under high vacuum to give pure product (5.35 grams, 95% yield with >99% purity).

Comparative Example B

Non-Aqueous Process, Outside the Scope of the Invention:

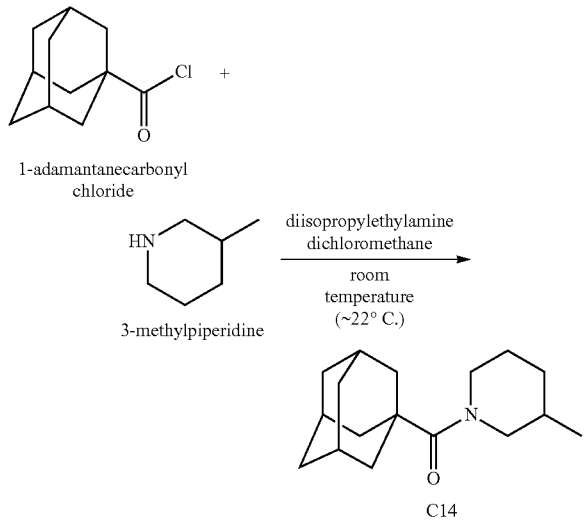

Diisopropylethylamine (18.4 milliliters, 0.11 moles) was added to a solution of 1-adamantylcarbonyl chloride (20 grams, 0.10 moles) and 3-methylpiperidine (12.5 milliliters, 0.11 moles) in dichloromethane (170 milliliters) and the solution stirred at room temperature for 16 hr. At this time, thin layer chromatography [15:85 ethyl acetate:hexane, 20 microliter aliquot into t-butylmethyl ether:1 N hydrochloric acid (400 microliters:400 microliters)] showed the formation of a single product and small amounts of starting material remaining. The solution was washed with 0.1N hydrochloric acid (50 milliliters), saturated sodium bicarbonate solution (50 milliliters), saturated sodium chloride solution (50 milliliters), dried using sodium sulfate, filtered and the solvents removed to give crude product which was further purified by flash chromatography on silica gel using 15:85 ethyl acetate:hexane to give pure product (23.7 grams, 90% yield with >99% purity).

It can be seen that room-temperature process (Comparative Example A) took much longer compared to the inventive process: 24 hours instead of 15 minutes. The non-aqueous process also took much longer than the inventive process (16 hours instead of 15 minutes), involved the use of organic solvents, resulted in decreased yield and was harder to purify.

The invention claimed is:

1. A process of making an adamantanamide, the process comprising the steps:
   i. mixing 0.9 to 1 molar equivalents of an alkylamine and 1.0-1.5 molar equivalents of a base in sufficient water to obtain a concentration of the alkylamine in the aqueous solution between 0.1 to 1.0 M and the pH between 8 to 14;
   ii. heating the mixture to a temperature in the range of from 50° C. to 90° C., to obtain a heated aqueous basic solution of the alkylamine;
   iii. adding 1 molar equivalent of adamantanecarbonyl chloride to the heated aqueous basic solution of alkylamine, to obtain a bi-phasic mixture;
   iv. stirring the bi-phasic mixture of the alkylamine and the adamantanecarbonyl chloride and maintaining the temperature in the range of from 50° C. to 90° C., until the reaction is completed;
   v. stirring and allowing the reaction mixture to cool to below 30° C., to precipitate the adamantanamide product out of the reaction mixture; and
   vi. separating the adamantanamide product from the reaction mixture.

2. The process according to claim 1, wherein the process further comprises an additional step, wherein residual adamantanecarboxylic acid salt in the reaction mixture is recycled and converted to adamantanecarbonyl chloride.

3. The process according to claim 1 or claim 2 wherein the base is an inorganic base.

4. The process according to claim 3 wherein the base selected from the group consisting of alkali metal hydroxides, carbonates, and mixtures thereof.

5. The process according to claim 3 wherein the base is sodium hydroxide.

6. The process according to any one of claims 1 to 5 wherein, wherein the temperature is in the range of from 55° C. to 80° C.

7. The process according to any one of claims 1 to 6 wherein the pH in step (i) is in the range of from 10 to 12.

8. The process according to any one of claims 1 to 7 wherein the reaction completion takes from 15 minutes to 2 hours.

9. The process of any one of claims 1 to 8 wherein adamantanecarbonyl chloride added in step (iii) has been pre-melted.

10. The process of any one of claims 1 to 8 wherein adamantanecarbonyl chloride added in step (iii) is added gradually, as a solid.

* * * * *